United States Patent [19]

Ito et al.

[11] Patent Number: 5,019,393
[45] Date of Patent: May 28, 1991

[54] BIOCOMPATIBLE SUBSTANCE WITH THROMBORESISTANCE

[75] Inventors: Ralph K. Ito, Quincy; Frank W. LoGerfo, Belmont, both of Mass.

[73] Assignee: New England Deaconess Hospital Corporation, Boston, Mass.

[21] Appl. No.: 227,728

[22] Filed: Aug. 3, 1988

[51] Int. Cl.⁵ .......................... A61F 2/00; A61K 9/22
[52] U.S. Cl. .................................. 424/423; 424/422; 424/424; 424/425; 424/426; 523/112; 523/113; 604/890.1; 604/266; 530/300
[58] Field of Search ............................... 424/422–426, 424/448; 523/112, 113; 604/266, 890.1; 530/300

[56] References Cited

U.S. PATENT DOCUMENTS

| | | | |
|---|---|---|---|
| 4,116,898 | 9/1978 | Dudley et al. | 523/112 |
| 4,273,873 | 6/1981 | Sugitachi et al. | 424/422 X |
| 4,378,803 | 4/1983 | Takagi et al. | 523/112 X |
| 4,447,562 | 5/1984 | Ivani | 423/113 X |
| 4,521,564 | 6/1985 | Solomon et al. | 523/112 X |
| 4,563,485 | 1/1986 | Fox, Jr. et al. | 523/113 |
| 4,594,407 | 6/1986 | Nyilas et al. | 523/113 X |
| 4,600,652 | 7/1986 | Solomon et al. | 523/112 X |
| 4,713,446 | 12/1987 | DeVore et al. | 523/113 X |
| 4,720,512 | 1/1988 | Hu et al. | 523/112 |
| 4,828,561 | 5/1989 | Woodroof | 424/422 X |

FOREIGN PATENT DOCUMENTS 2164343  3/1986  United Kingdom ............... 523/113

Primary Examiner—Thurman Page
Assistant Examiner—G. S. Kishore
Attorney, Agent, or Firm—Lahive & Cockfield

[57] ABSTRACT

Disclosed is a biocompatible, thromboresistant substance useful for implantable and extracorporeal devices in contact with the vascular system, and methods for producing the same. The biocompatible, thromboresistant substance comprises a synthetic, biocompatible material, at least one biocompatible base coat layer adhered to at least one surface of the material, and a thrombogenesis inhibitor immobilized on the base coat layer via a component capable of binding the inhibitor. The thrombogenesis inhibitor is streptokinase, urokinase, tissue plasminogen activator, ATPase, 5'-nucleotidase, and active fragments and active analogs thereof.

37 Claims, 2 Drawing Sheets

BIOCOMPATIBLE SUBSTANCE WITH THROMBORESISTANCE

CROSS-REFERENCE TO RELATED APPLICATION

The subject matter of this application is related to applicants' copending application Ser. No. 227,700, entitled "HIRUDIN-COATED BIOCOMPATIBLE SUBSTANCE", filed on even date herewith.

BACKGROUND OF THE INVENTION

The technical field of the present invention is prosthetic vascular materials, and more specifically is biocompatible, thromboresistant substances and methods of their preparation.

Exposure of blood to artificial surfaces usually leads to deposition of a layer of adherent platelets, accompanied by activation of the intrinsic coagulation system, and ultimately to the formation of a thrombus. In fact, significant blood/materials interaction can occur on a single pass through a prosthetic arterial graft. The types of blood proteins initially adsorbed or bound to synthetic surfaces may include proteins involved in contact coagulation. Contact coagulation or the extrinsic pathway of coagulation is a complex pathway of biochemical events that induces fibrin formation, platelet and complement activation, chemotaxis, kinin generation, and activation of fibrinolytic components. In addition, each of these events augments subsequent biochemical pathways often controlled by positive and negative feedback loops. Thus, thrombosis induced by contact with artificial materials is a major obstacle in the development and use of internal prostheses and extracorporeal devices such as artificial vessels and organs, and cardiopulmonary bypass and hemodialysis equipment.

Materials having varying degrees of thromboresistance have been utilized in vascular prostheses with limited success. These materials include corroding (self-cleaning) metals, synthetic polymers such as polydimethyl siloxane, Teflon, acylates and methacrylates such as Dacron, electrets, anionic copolymers, and hydrogels for a review see Salzman et al. (1987) in *Hemostasis and Thrombosis, Basic Principles and Clinical Practice* (Colman et al., eds.) J. B. Lippincott Co., Phila., Pa., pp. 1335–1347).

To decrease the chances of thrombosis due to extended periods of contact with such artificial materials, patients have been treated with systemically administered anti-coagulant, anti-platelet, and thrombolytic drugs. These include any compound which selectively inhibits thromboxane synthetase without affecting prostacycline synthetase, affects platelet adherence as well as aggregation and release, enhances vascular PGI2 production, and/or inhibits both thrombin- and thromboxane-mediated platelet aggregation. Such compounds include aspirin, sulfinpyrazone, dipyridamole, ticlopidine, and suloctidil. However, treatment with these drugs often elicits unwanted side effects including systemic hemmorhaging and the inability to initiate and complete desired clotting elsewhere in the body.

To improve on the thromboresistance of artificial materials, biologically active molecules having thrombolytic, anticoagulating, thrombogenesis-inhibiting, and/or platelet inhibiting abilities have been linked thereto. For example, heparin has been bound to artificial surfaces to reduce cooagulation by activating variuous inhibitors of the intrinsic clotting system (Salzman et al. (1987) in *Hemostasis and Thrombosis: Basic Principles and Clinical Practice.* 2nd Ed., (Colman et al., eds.), Lippincott Co., Phila., Pa., pp. 1335–1347). However, heparin enhances platelet responses to stimuli such as ADP or collagen, and promotes two adverse primary blood responses towards synthetic surfaces: platelet adhesion and aggregation. In addition, although surface-bound heparin/antithrombin complex may be passive towards platelets, the wide variety of effects it has on interactions with endothelial cell growth factor, inhibition of smooth muscle proliferation, and activation of lipoprotein lipase raises questions as to what adverse effects it may induce over time.

Anti-platelet agents such as $PGE_1$, $PGI_2$ (experimental use only), cyclic AMP, and aspirin have also been attached to solid polymer surfaces. These agents discourage the release of platelet factors that stimulate adverse healing responses in the vicinity of a vascular graft. They may also reduce platelet-aided thrombus formation by inhibiting platelet adhesion.

The exposure of many artificial surfaces to albumin prior to vascular contact results in reduced reactivity with platelets (NIH Publication No. 85-2185, Sept., 1985, pp. 19–63). Therefore, albumin has been used to coat extracorporeal surfaces before cardiopulmonary by-pass surgery. However, long-term thermoresistance has not been achieved by this procedure.

Fibrinolytically active streptokinase and urokinase, alone or in combination with heparin have been attached to artificial surfaces by Kusserow et al (Trans. Am. Soc. Artif. Intern. Organs (1971) 17:1). These enzymes reduce excessive fibrin deposition and/or thrombotic occlusions. However, the long term assessment of their ability to confer thromboresistance to a synthetic surface has not been determined.

Surface active agents such as Pluronic F-68 have also been immobilized on artificial surfaces, but do not appear to offer long term blood compatibility (Salyer et al. (1971) *Medical Applications of Plastics.* Biomed. Materials Res. Sym. (Gregor, ed.) No. 1 pp. 105).

Therefore, what is needed are better biocompatible materials which are thromboresistant in the long term and whose active components do not cause detrimental side affects.

An object of the present invention is to provide a synthetic, biocompatible, thromboresistent material useful for implantable and extracorporeal devices in contact with bodily fluids.

Another object is to provide an immobilized thrombogenesis inhibitor which is biologically active, and a method of preparing the same.

Still another object of this invention is to provide a method of inhibiting platelet aggregation, the release of platelet factors, and thrombogenesis at the localized site of the graft or prosthesis-blood interface, thus avoiding the systemic effect of antiplatelet and antithrombosis drugs.

SUMMARY OF THE INVENTION

Materials and methods are disclosed herein for the provision of biocompatible, thromboresistant substances useful as a component of implantable or extracorporeal devices in contact with the blood.

It has been discovered that a synthetic, biocompatible material can be made into a thromboresistant substance by immobilizing to it, by way of a base coat layer, a thrombogenesis inhibitor other than hirudin, or an active analog or fragment thereof, in such a way that does not compromise its thrombogenesis inhibiting activity.

The term "thrombogenesis inhibitor" is used herein to describe molecules which interfere with or inhibit the formation of a thrombus. Such molecules include those which interfere or inhibit the intrinsic and extrinsic coagulation system, platelet adherence, aggregation, or factor release or activity, or the release or active of tissue factors. Included are native, synthetic, or recombinant proteins, or active analogs, fragments, derivatives, or fusion products thereof, and mixture thereof which can interfere and inhibit the formation of a thrombus. Thrombogensis inhibitors useful for imparting thromboresistance to the substance include proteins which are mambrane-bound in their native state (e.g., adenosine triphosphatase (ATPase), adenosine diphosphatase (ADPase), and 3'-nucleotidase), and those which are normally soluble in vivo (e.g., tissue plasminogen activator (tPA), urokinase (UK), and streptokinase (SK)). However, other molecules which inhibit or interfer with the activity of other thrombogenesis inhibitors are useful as well.

Synthetic materials contemplated by the instant invention are preferably polymers such as Dacron, nylon, polyurethane, cross-linked collagen, polytetrafluoroethylene, polyglycolic acid, and mixtures thereof, the most preferred polymeric material being Dacron. Other synthetic materials might also be used.

At least one layer of biocompatible material is adhered to at least one surface of the synthetic material. This base coat layer contains a component which is capable of binding the thrombogenesis inhibitor. Examples of such base coat components include proteins, peptides, lipoproteins, glycoproteins, glycosaminoglycans, hydrogels, synthetic polymers, and mixtures thereof. In preferred aspects of the invention, the base coat layer includes a protein component such as serum albumin or fibronectin from, for example, human or bovine sources, or mixtures of these proteins. Other materials might also be used to form the base coat layer.

In accordance with the invention, the thrombogenesis inhibitor is immobilized on the synthetic material via a base coat layer which is adhered to least one surface cf the synthetic material. The base coat layer contains a component capable of binding the thrombogenesis inhibitor without compromising the biological activity of the inhibitor.

In exemplary aspects of the invention, the synthetic material is activated prior to having the base coat layer adhered thereto so as to enhances its ability to bind the base coat base layer. For example, in one preferred aspect, the synthetic material is contacted with a solution which makes available at least one chemically active group (e.g., a carboxylic acid group) in the material for binding to a bifunctional cross-linking reagent (e.g., carbodiimide). The material so treated is then put into contact with a solution containing the cross-linking carbodiimide reagent for a time sufficient to allow the chemically active group to bind thereto.

In another embodiment, the synthetic material may be contacted with a solution which removes impurities therein and/or thereon prior to the activation step described above.

The immobilization step may be carried out by initially contacting the thrombogenesis inhibitor with at least one molecule of a bifunctional cross-linking reagent for a time sufficient to allow linking of the reagent to the inhibitor, and then binding the thrombogenesis inhibitor-linked reagent to the base coat. The bound thrombogenesis inhibitor retains its thrombogenesis inhibiting activity when bound to the reagent. The bifunctional cross-linking reagent useful for such an immobilization step may be heterobifunctional (e.g., N-succinimidyl 3-(2-pyridyldithio)propionate (SPDP)), homobifunctional (e.g., ethylene glycolbis (succinimidylsuccinate) (EGS)), or a mixture of both.

The term "bifunctional cross-linking reagent" is defined herein as a molecule having the ability to bind to, and therefore link, two reactive groups on, for example, one molecule or two separate molecules. If the bifunctional cross-linking reagent binds two different types of groups, it is a "heterobifunctional" cross-linking reagent. However, if the bifunctional cross-linking reagent binds only to two similar groups, it is "homobifunctional".

Prior to the binding step, the thrombogenesis-linked reagent may be subjected to chromatographic procedures to remove impurities mixed in with it.

In an alternative aspect of the invention, the base coat adhered to the synthetic material may be linked at the same time to at least one molecule of a bifunctional cross-linking reagent. In this embodiment, the method further includes binding the thrombogenesis inhibitor-linked reagent to the base coat-linked reagent, thereby linking the thrombogenesis inhibitor to the material-adhered base coat layer.

In another aspect of the invention, the base coat-linked reagent is reduced prior to the binding step. Reduction results in the formation of sulhydryl groups from the reagent on the base coat which can react with the inhibitor-linked bifunctional cross-linking reagent via a substitution reaction to form an S—S bond, thereby covalently linking the thrombogenesis inhibitor to the base coat.

In yet another aspect of the invention, the base coat is linked to the thrombogenesis inhibitor before it is linked to the synthetic, biocompatible material.

The invention will next be described in connection with certain illustrated embodiments. However, it should be clear that various modifications, additions, and deletions can be made without departing from the spirit or scope of the invention.

BRIEF DESCRIPTION OF THE DRAWING

The foregoing and other objects of the present invention, the various features thereof, as well as the inventions thereof may be more fully understood from the following description when read together with the accompanying drawings in which.

DESCRIPTION OF THE INVENTION

Figure 1:
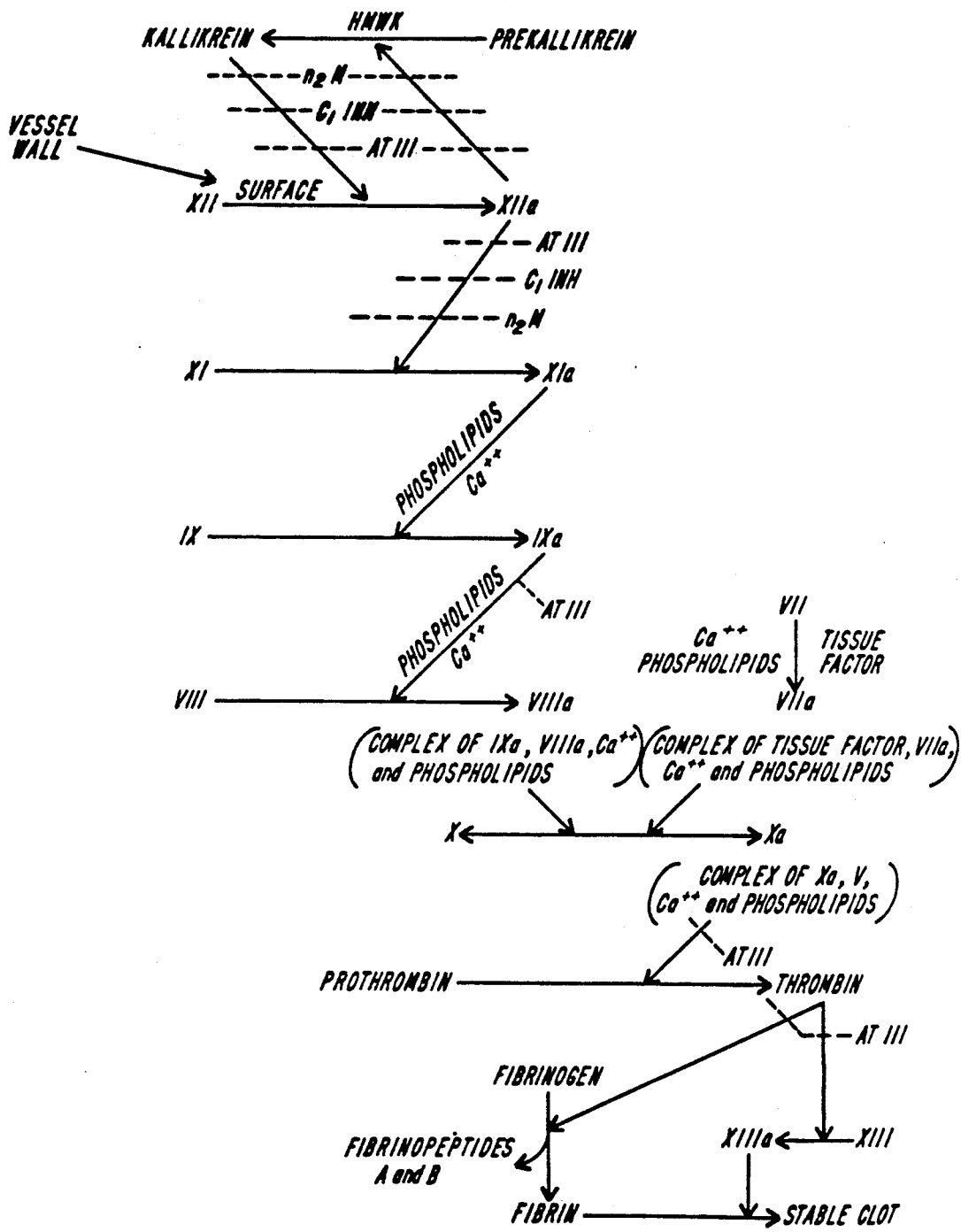
FIG. 1 is a diagrammatic representation of the pathways involved in thrombogenesis.

This invention provides biocompatible, thromboresistant substances useful for implantable and extracorporeal devices in contact with the vascular system, and methods for their fabrication.

The substances provided by this invention include a synthetic biocompatible substance having a thrombogenesis-inhibiting reagent linked thereto via a biocompatible base coat adhered to the material's surface.

The material useful in a prosthetic extracorporeal or implantable device may be composed of any biocompatible, synthetic, preferably polymeric material having enough tensile strength to withstand the rigors of blood circulation, and having groups onto which a base coat can be directly or indirectly bound. Examples of such synthetic materials are polytetrafluoroethylene (Teflon) and Dacron, nylon, and the like. The material may have any dimensions suitable for the purpose for which it is being used. For example, it may be an integral part of an implanted heart valve or of an extracorporeal device used for hemodialysis or cardiopulmonary by-pass surgery, or it may be used to coat catheters or to line the interior of a vascular graft.

The synthetic material, when obtained, may be coated with or contain various noncovalently adhered impurities whose removal may be prerequisite for the adherence of a base coat thereto. For example, lubricants on commercial quality Dacron can be removed by contacting the Dacron with a solution containing, for example, various detergents, solvents, or salts, which loosen and/or solubilize these impurities.

TABLEs 1 and 2 outline representative methods of preparing the biocompatible, thromboresistant substance, where "Da" refers to a synthetic material composed of woven Dacron fibers, and "HSA" refers to human serum albumin.

TABLE 1

| STEP | PROCESS |
| --- | --- |
| (1) | Da. + NaOH → Da-COOH |
| (2) | Da-COOH + EDC → Da-EDC |
| (3) | Da-EDC + HSA → Da-HSA + urea (EDC by-product) |
| (4) | Da-HSA + SPDP → Da-HSA-SPDP |
| (5) | Da-HSA-SPDP + DTT → Da-HSA-SH + P-2-T |
| (6) | Inhibitor + SPDP → Inhibitor-SPDP |
| (7) | Da-HSA-SH + Inhibitor-SPDP → Da-HSA-S-S-Inhibitor + P-2-T |

TABLE 2

| STEP | PROCESS |
| --- | --- |
| (1) | HSA + SPDP → HSA-SPDP |
| (2) | HSA-SPDP + DTT → HSA-SH + P-2-T |
| (3) | Inhibitor + SPDP → Inhibitor-SPDP |
| (4) | HSA-SH + Inhibitor-SPDP → HSA-S-S-Inhibitor + P-2-T |
| (5) | Da + NaOH → Da-COOH |
| (6) | Da-COOH + EDC → Da-EDC |
| (7) | Da-EDC + HSA-S-S-Inhibitor → Da-HSA-S-S-Inhibitor + urea (EDC by-product) |

Initially, the material may be activated so as to enhance the binding of the base coat layer. This activating step increases the number of chemically active groups in the material. For example, alkaline hydrolysis may be performed to increase the number of reactive carboxylic acid groups in the Dacron to which a bifunctional cross-linking reagent such as carbodiimide may be bound. Ultimately, the base coat will adhere to the bound carbodiimide groups on the material. However, this method must be performed with care, as alkaline hydrolysis partially degrades the Dacron, resulting in a fraying of the material's fibers.

At least one base coat layer is adhered to at least one surface of the synthetic material.

This layer, either adhered to the material or unbound, provides components for attachment of the thrombogenesis inhibitor. Such components provide more binding sites for the inhibitor than the synthetic material, alone, thereby amplifying the amount of inhibitor which may be bound. Useful components include proteins, peptides, lipoproteins, glycoproteins, glycosaminoglycans, synthetic polymers, and mixtures thereof. Proteins such as serum albumin and fibronectin are particularly useful for this purpose as they are known to have antithrombogenic properties, themselves, are very desirable as base coat components (Lyman et al. (1965) Trans. Am. Soc. Artif. Intern. Organs 11:301; Falb et al. (1971) Fed. Proc. 30: 1688). An HSA molecule, for example, has 65 amino groups available as binding sites.

Attachment of the base coat to the artificial surface may be covalent in nature. Methods to covalently bind proteins to Dacron involve attack of the free reactive succinimide ester group of the cross-linking reagent to primary amino groups on a protein. As shown in the example in Table 1, to covalently adhere the base coat to Dacron, the Dacron is initially treated with 0.5 N NaOH and reacted with carbodiimide before it is coated with HSA (base coat) in phosphate buffered saline (PBS).

A thrombogenesis inhibitor useful as a coating for surfaces in contact with blood, bodily fluids, or tissues, is then covalently adhered to the base coat via the component. Inhibitor-coated substances are ideal for implantable use in devices which are in direct contact with blood. For example, by-pass grafts used to replace blood vessels often become filled with blood clots or thrombi, resulting in restricted blood flow. Since the inhibitor-coated substance is resistant to formation of blood clots, thrombosis and subsequent blockage of the bypass graft will be prevented. Likewise when catheters are placed into the vascular system for a diagnostic or therapeutic purposes, a blood clot often forms on the outside of the catheter. The clot may be washed off the catheter by flowing blood, or be jarred loose by manipulation of the catheter, increasing the possibility of embolism and blockage of the circulation to vital organs. Inhibitor-coated substances provide similar advantages for artificial or prosthetic heart valves, intraaortic balloon pumps, total or artificial heart or heart assist devices, intracaval devices, and any device in contact with the bloodstream. In addition, inhibitor-coated devices provide advantages for intracavity devices such as intraperitoneal dialysis catheters and subcutaneous implants where the thrombin-induced inflammmatory reactions would be diminished.

Thrombogenesis inhibitors useful for these purposes include molecules which interfere with, or inhibit thrombogenesis. These include ATPase, ADPase, 5'-nucleotidase, streptokinase, urokinase, tissue plasminogen activator, anticoagulants, platelet inhibitors (e.g., prostacycline and aspirin), and active analogs, fragments, derivatives, and fusion products thereof, or mixtures thereof.

ADPase reduces platelet aggregation by degrading ADP. ADP is stored in the dense granules of platelets and can be released by thrombin, epinephrine, collagen, and other stimulants. When released, ADP promotes platelet receptor binding to fibrinogen and to von Willebrand Factor, two proteins essential for aggregation, and then promotes thromboxane synthesis, platelet aggregation, more ADP release, and thus, self-enhances platelet aggregation.

ATPase catalyzes the conversion of ATP to ADP, which can then be acted upon by ADPase, as described above.

Figure 2:
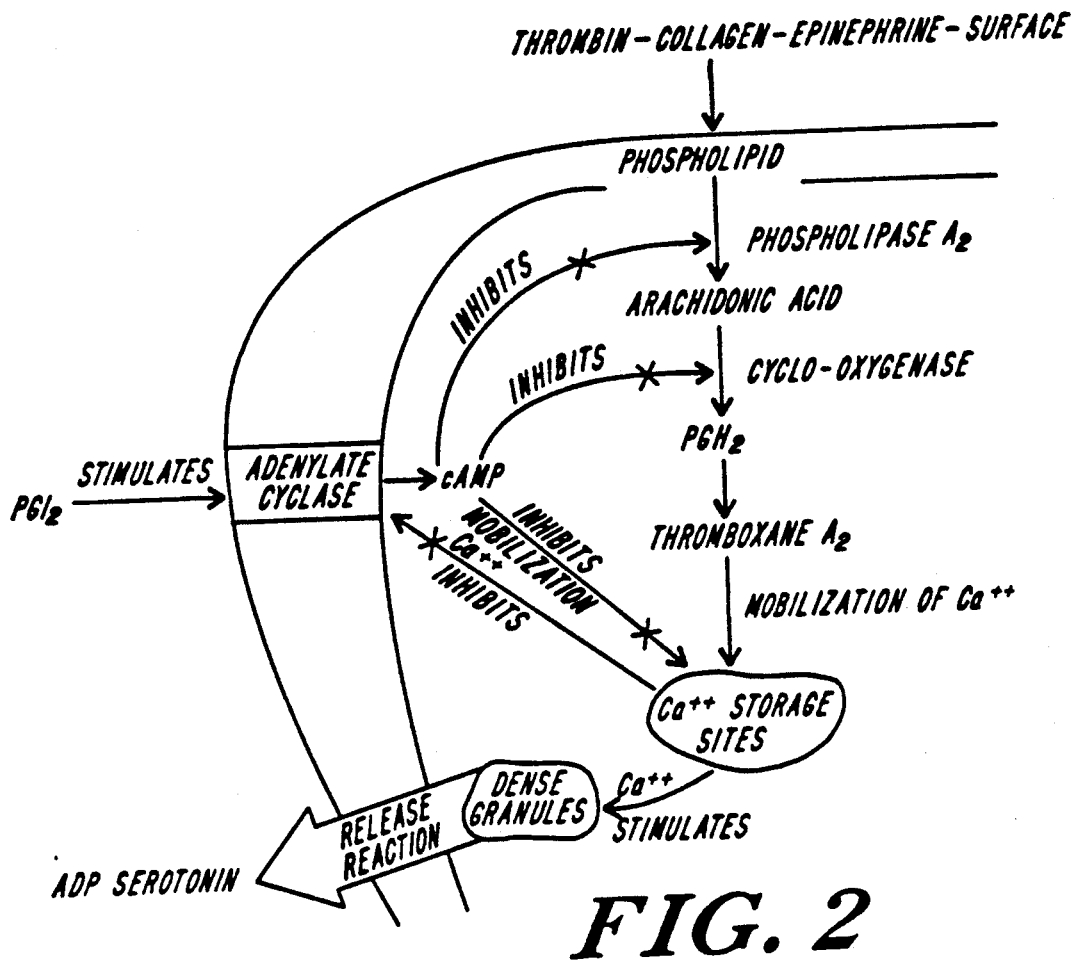
FIG. 2 is a diagrammatic representation of platelet involvement in thrombogenesis.

5'-nucleotidase (AMPase), like ADPase, degrades ADP. It also degrades AMP, a competitive antagonist for ADP receptor birding, to adenosine, a platelet inhibitor. Adenosine inhibits platelet aggregation by increasing intracellular levels of cyclic AMP. High levels of cyclic AMP inhibit mobilization of calcium ions from platelet storage pools. Free calcium ions within the platelet stimulates release of additional ADP from platelet dense granules, and is necessary for platelet aggregation, hence thrombogenesis (see FIG. 2).

The thrombogenesis inhibitor is directly or indirectly immobilized on the base coat via the use of a bifunctional cross-linking reagent. In particular, a heterobifunctional cross-linking reagent which has two different reactive groups at each end of a linear molecule, and can therefore bind two different reactive groups on other molecules or on a different region of the same molecule, is most useful as a bifunctional cross-linking agent. For example, photoreactive cross-linkers, such as sulfosuccinimidyl 2-(m-azodo-o-nitro-benzamido)ethyl-1, 3'-dithio-propionate (SAND), or N-succinimidyl-6-(4;azoido-2'-nitrophenyl-amino) hexanoate (SANPAH) have a photoreactive group that can directly insert into C—H bonds of the base coat by photochemical coupling, while the other group remains free to bind to proteins.

Other useful and preferable cross-linking reagents (such as SPDP) and their characteristics are found in TABLE 3. In TABLE 3, the "Double-Agent Number" listed for each reagent is the commercial designation for the reagent as made available by Pierce Chemical Co. (Rockford, Ill.).

TABLE 3

| CROSS-LINKING REAGENTS (part A) | | | | | | |
|---|---|---|---|---|---|---|
| Double-Agent Number | Double-Agent Acronym | Bifunctionality | | Reactive towards: | | |
| | | Homo | Hetero | NH$_2$ | SH | Photo-Reactive |
| 21551 | ANB-NOS | | X | X | | X |
| 20106 | APB | | X | | X | X |
| 20107 | APG | | X | | | X |
| 21559 | APTP | | X | X | | X |
| 21579 | BS$^3$ | X | | X | | |
| 22319 | BMH | X | | | X | |
| 21554 | BSOCOES | X | | X | | |
| 21524 | DFDNB | X | | X | | |
| 20047 | DIDS | X | | X | | |
| 21664 | DMA | X | | X | | |
| 20666 | DMP | X | | X | | |
| 20668 | DMS | X | | X | | |
| 22585 | DSP | X | | X | | |
| 21555 | DSS | X | | X | | |
| 20590 | DST | X | | X | | |
| 20665 | DTBP | X | | X | | |
| 22590 | DTBPA | X | | | | X |
| 21577 | DTSSP | X | | X | | |
| 21550 | EADB | | X | X | | X |
| 21565 | EGS | X | | X | | |
| 23700 | FNPA | | X | X | | X |
| 21560 | HSAB | | X | X | | X |
| 26095 | MABI | | X | X | | X |
| 22310 | MBS | | X | X | X | |
| 27715 | NHS-ASA | | X | X | | X |
| 20669 | PNP-DTP | | X | X | | X |
| 21552 | SADP | | X | X | | X |
| 21549 | SAND | | X | X | | X |
| 22588 | SANPAH | | X | X | | X |
| 27716 | SASD | | X | X | | X |
| 22325 | SIAB | | X | X | X | X |
| 22320 | SMCC | | X | X | X | |
| 22315 | SMPB | | X | X | X | |
| 21557 | SPDP | | X | X | X | |
| 21556 | Sulfo-BSOCOES | X | | X | | |
| 20591 | Sulfo-DST | X | | X | | |
| 21556 | Sulfo-EGS | X | | X | | |
| 22312 | Sulfo-MBS | | X | X | X | |
| 21553 | Sulfo-SADP | | X | X | | X |
| 22589 | Sulfo-SANPAH | | X | X | | X |
| 22327 | Sulfo-SIAB | | X | X | X | |
| 22322 | Sulfo-SMCC | | X | X | X | |
| 22317 | Sulfo-SMPB | | X | X | X | |
| 26101 | TRAUT'S | X | | X | | |

| CROSS-LINKING REAGENTS (part B) | |
|---|---|
| Agent Acronym | Chemical Name |
| ANB-NOS | N-5-azido-2-nitrobenzoyloxysuccinimide |
| APB | p-azidophenacyl bromide |
| APG | P-azidophenyl glyoxal |
| APTP | n-4-(azidophenylthio)phthalimide |
| BS$^3$ | bis(sulfosuccinimidyl) suberate |
| BMH | bis maleimidohexane |
| BSOCOES | bis[2-(succinimidooxycarbonyloxy)-ethyl]sulfone |
| DFDNB | 1,5-difluoro-2,4-dinitrobenzene |
| DIDS | 4,4'-diisothiocyano-2,2'-disulfonic acid stilbene |
| DMA | dimethyl adipimidate-2 HCl |
| DMP | dimethyl pimelimidate-2 HCl |
| DMS | dimethyl suberimidate-2 HCl |
| DSP | dithiobis(succinimidylpropionate) |
| DSS | disuccinimidyl suberate |
| DST | disuccinimidyl tartarate |
| DTBP | dimethyl 3,3'-dithiobispropionimidate-2-HCl |
| DTBPA | 4,4'-diothiobisphenylazide |
| DTSSP | 3,3-dithiobis(sulfosuccinimidyl-propionate) |
| EADB | ethyl-4-azidophenyl 1,4-dithio-butyrimidate |
| EGS | ethylene glycolbis(succinimidyl-succinate |
| FNPA | 1-azido-4-fluoro-3-nitrobenzene |
| HSAB | N-hydroxysuccinimidyl-4-azidobenzoate |
| MABI | methyl-4-azidobenzoimidate |
| MBS | m-maleimidobenzoyl-N-hydroxysulfo-succinimide ester |
| NHS-ASA | N-hydroxysuccinimidyl-4-azidosalicylic acid |
| PNP-DTP | p-nitrophenyl-2-diazo-3,3,3-trifluoro-propionate |
| SADP | N-succinimidyl(4-axidophenyl)-1,3'-dithiopropionate |
| SAND | sulfosuccinimidyl 2-(m-azido-o-nitro-benzamido)-ethyl-1,3'-dithiopropionate |
| SANPAH | N-succinimidyl-6(4'-azido-2'-nitro-phenyl-amino)hexanoate |
| SASD | sulfosuccinimidyl 2-(p-azidosalicyl-amido)ethyl-1,3'-dithio-propionate |
| SIAB | N-succinimidyl(4-iodoacetyl)amino-benzoate |
| SMCC | succinimidyl 4-(N-maleimidomethyl)-cyclohexane-1-carboxylate |
| SMPB | succinimidyl 4-(p-maleimidophenyl)-butyrate |
| SPDP | N-succinimidyl 3-(2-pyridyldithio) propionate |
| Sulfo-BSOCOES | bis[2-(sulfosuccinimidooxy-carbonyl-oxy)ethyl]sulfone |
| Sulfo-DST | disulfosuccinimidyl tartarate |

TABLE 3-continued

| | |
|---|---|
| Sulfo-EGS | ethylene glycolbis(sulfosuccinimidyl-succinate) |
| Sulfo-MBS | m-maleimidobenzoyl-N-hydro-xysulfo-succinimide ester |
| Sulfo-SADP | sulfosuccinimidyl(4-azidophenyldithio)-propionate |
| Sulfo-SANPAH | sulfosuccinimidyl 6-(4'azido-2'-nitro-phenylamino)hexanoate |
| Sulfo-SIAB | sulfosuccinimidyl(4-iodoacetyl)amino-benzoate |
| Sulfo-SMCC | sulfosuccinimidyl 4-(N-maleimido-methyl)cyclohexane-1-carboxylate |
| Sulfo-SMPB | sulfosuccinimidyl 4-(p-maleimido-phenyl)butyrate |
| TRAUT'S | 2-iminothiolane-HCl |

The cross-linking reagent is applied to the base coat in amounts such that the desired binding site density is achieved. Binding site density is that amount of cross-linking reagent, in terms of moles/g synthetic material, to bind to the base coat while providing confluent coverage of the surface.

To put the inhibitor in condition for linkage to the base coat, the cross-linking reagent may be initially coupled separately to both the base coat and to the inhibitor. The kinetic constants of the inhibitors are compared before and after coupling to evaluate effects of the procedure on their kinetic constants. The inhibitor should remain biologically active after being coupled. Therefore, standard activity assays specific for the inhibitor to be immobilized are performed using a standard thrombin solution to evaluate this capacity.

The protein component of, the base coat may be bound to the thrombogenesis inhibitor forming a conjugate prior to its adherence to the synthetic material. The conjugate can then be bound to the synthetic material as described for base coat binding to achieve the same effect (TABLE 2). In addition, the thrombogenesis inhibitor conjugate retains biological activity, and can be used as an agent to increased half life in the circulation as it is not easily cleared by the kidney.

SPDP will react with terminal as well as epsilon amino groups, Since derivatization of a terminal amino group can inactivate a biologically active protein, T-BLOCK (Pierce Chemical Co., Rockford, Ill.) may be used to block that group during SPDP-derivatization. The T-BLOCK is then removed after derivatization to restore biological activity.

The invention will be further understood from the following, non-limiting examples.

EXAMPLE 1: Streptokinase (SK) Immobilization

A. Pretreatment and Activation of Dacron

Dacron polyester 52 (DuPont) is sectioned into 1.0 cm lengths. The lubricant on and in the woven surface is removed by washing once for 1 hr with carbon tetrachloride, and twice with 100% $CH_3OH$. The methanol is removed by multiple water washes, followed by one wash in phosphate buffered saline, pH 7.4 (PBS).

The graft material is then subjected to alkaline hydrolysis to increase available COOH groups. The material is treated with 0.5 M NaOH at 50° C. for 1 hr. It is then washed with $H_2O$ repeatedly, and the following steps initiated immediately.

B. Carbodiimide Derivatization of Activated Dacron

The activated material is placed into 100.0 ml of 10 mM water-soluble carbodiimide (EDC) in deionized water, pH 4.6–5.0, for 1 hour at RT with constant stirring. The material is removed and washed in PBS, to remove excess unbound EDC.

C. Base Coat Formation

The base coat is applied to the lumen of the Dacron graft material. The derivatized Dacron material is incubated in a 5% HSA solution in PBS at 1 ml/$cm^2$ graft material for 24 hr at RT with constant stirring. The graft is removed and washed in PBS to remove non-specifically bound HSA. Approximately 20 mg protein/mg Dacron is covalently bound.

D. Linkage of SPDP to the Base Coat

The HSA-bound Dacron material is incubated in a 1.0 mM solution of SPDP in PBS, pH 7.4, to bind SPDP to the HSA (100 mM SPDP/$cm^2$ base coat). Incubation is terminated after 30–40 min at RT. The graft is washed with PBS to remove nonspecifically bound SPDP.

E. Activation of SPDP on Base Coat and Measurement of Binding Site Density

The SPDP-linked material is dried and weighed to obtain its absolute weight. It is then placed in a 50 mM solution of dithiotreitol (DTT) for 5 min at RT. This reaction releases pyridine-2-thione (P-2-T) from the bound SPDP and simultaneously forms free sulphydryl (SH) groups on the base coat. The released P-2-T is quantitated by absorption spectrophotometry at 343 nm using its extinction coefficient ($E = 8.08 \times 10^3$), and is directly proportional to the quantity of bound SPDP or binding sites. The number of binding sites are calculated and expressed as moles of sites/g of Dacron.

The material is then washed 5 times in PBS and 4 times in $dH_2O$.

F. Linkage of SK to Cross-linker

Albumin-free SK (KabiVitrum, Stockholm, Sweden) is filter-transfered with use of a PD-10 column (Pharmacia, Piscataway, N.J.) to remove contaminants and amino acid preservatives, and to transfer SK into 0.1 M PBS buffer, pH 7.5. 0.5 ml fractions are collected, absorbance values at 280 nm recorded, and desired fractions pooled. The molar concentration of pooled SK is determined using its absorptivity coefficient at 280 nm ($A_{280}$ 1.0%/1.0 cm = 7.5). The concentration of pooled SK is then set to approximately 0.1 mM in PBS buffer. A 20 mM SPDP solution is prepared in absolute ethanol just prior to use and mixed with SK in various mole to mole ratios (i.e., 1:10). The mixture is allowed to incubate for 30 min at 23° C. It is then filter-transferred into PBS buffer, pH 7.5 using a PD-10 column equilibrated with PBS buffer, pH 7.5. 0.5 ml fractions are collected, absorbance measurements at 280 nm recorded, and desired fractions (i.e., $A_{280}$ greater than 1.8) pooled. The pool contains SK linked to 2-pyridine disulphide (SK-2-PD) in PBS buffer, pH 7.5.

G. Measurement of SPDP Bound to SK

The binding of SPDP to SK can be quantitated by the addition of DTT which liberates pyridine-2-thione (P-2-T) from SPDP bound to SK, and which can be measured spectrophotometrically at 343 nm. From this measurement, the moles of SPDP bound to SK can be calculated. Each P-2-T released represents one covalent attachment of SPDP to SK. One mole of SK binds per 1.2 moles SPDP in the present studies.

H. Linkage of Derivatized SK to Basecoat

The reduced SPDP-linked base coat (having free SH groups) is washed with PBS to remove the DTT. SPDP-linked SK is then added to the graft at 50.0 mg/cm$^2$ Dacron. The solution is incubated overnight at RT to allow the binding of SPDP-SK to SH groups on the Dacron graft. The Dacron material with SK covalently immobilized thereto is then washed and stored in PBS.

I. Immobilized (SK) Activity Analysis

SK, when mixed with human plasminogen forms an active proteolytic complex that can be quantitated using the chromogenic substrate, S-2251 (KabiVitrum A.B., Stockholm, Sweden). A standard curve is constructed using known concentrations of SK (500-10,000 units/ml). A 60 ml aliquot of each standard is added to 120 ml of 0.2 mM human plasminogen (American Diagnostica, Greenwich, Conn.), and incubated at 37° C. for 10 min. SK-plasminogen complex is formed as well as free plasma which interferes with the analysis. This interference is eliminated by the addition of 60 ml of 2.0 mg/ml soybean trypsin inhibitor which inhibits all free plasma. The quantitative analysis of SK-plasminogen is accomplished by addition of 420 ml of 0.86 mM S-2251 in 50 mM Tris-HCl, 12 mM NaCl, pH 7.4, and monitoring the change in absorbance per min at 405 nM at 37° C. The immobilized SK is substituted for the standard solution in the assay. The measured activity of the material on S-2251 is then equated to the standard curve.

EXAMPLE 2: Urokinase (UK) Immobilization

A)-H) (Same as described for EXAMPLE 1 except that UK (Abbokinase, Abbot Chemical Co., Chicago, Ill.) is substituted for SK.)

I. Immobilized UK Activity Analysis

The activity of immobilized UK is evaluated against a standard curve generated using soluble UK in concentrations of from 10 to 1000 units of UK (refered here as CTA units). The chromogenic substrate, S-2444 (KabiVitrum AB, Stockholm, Sweden), is used at 0.3 mM to measure activity of UK standards by monitoring change in absorbance at 405 nm in 50.0 mM Tris, 12.0 mM NaCl, pH 8.8 at 37° C. A standard curve is thus generated. A section of material with immobilized or bonded UK is placed into the substrate under the same conditions, and the change in absorbance is recorded. The activity of the immobilized UK is evaluated by comparison to the activity of the standard curve.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A biocompatible substance with thromboresistance comprising:
   (a) a synthetic, polymeric, biocompatible material;
   (b) at least one biocompatible base coat layer adhered to at least one surface of said material; and
   (c) a thrombogenesis inhibitor immobilized on said base coat layer, said thrombogenesis inhibitor being other than hirudin or an active analog or fragment of hirudin,
   said base coat layer having a component capable of binding said thrombogenesis inhibitor.

2. The substance of claim 1 wherein said thrombogenesis inhibitor is an inhibitor selected from the group consisting of streptokinase, urokinase, tissue plasminogen activator, ATPase, ADPase, 5'-nucleotidase, and active fragments, and active analogs thereof, and mixtures thereof.

3. The substance of claim 1 wherein said polymer is selected from the group consisting of Dacron, nylon, polyurethane, cross-linked collagen, polyglycolic acid, polytetrafluoroethylene, and mixtures thereof.

4. The substance of claim 3 wherein said polymer comprises polyethylene terphthalate.

5. The substance of claim 1 wherein said base coat layer comprises a component selected from the group consisting of a protein, peptide, lipoprotein, glycoprotein, glycosaminoglycan, hydrogel, synthetic polymer, and mixtures thereof.

6. The substance of claim 5 wherein said component of said base coat layer comprises a protein.

7. The substance of claim 6 wherein said protein is selected from the group consisting of serum albumin, fibronectin, and mixtures thereof.

8. The substance of claim 7 wherein said protein comprises bovine serum albumin.

9. The substance of claim 7 wherein said protein comprises human serum albumin.

10. The substance of claim 7 wherein said protein comprises bovine fibronectin.

11. The substance of claim 7 wherein said protein comprises human fibronectin.

12. The substance of claim 1 further comprising at least one molecule of a bifunctional cross-linking reagent linking said thrombogenesis inhibitor to said base coat layer.

13. The substance of claim 12 wherein said bifunctional cross-linking reagent is heterobifunctional.

14. The substance of claim 12 wherein said bifunctional cross-linking reagent is homobifunctional.

15. The substance of claim 13 wherein said heterobifunctional cross-linking reagent comprises SPDP.

16. A method of producing a biocompatible, thromboresistant substance, said method comprising the steps of:
   (a) adhering at least one base coat layer to at least one surface of a synthetic, polymeric, biocompatible material, said base coat layer containing a component capable of binding said base coat layer thereto; and
   (b) immobilizing a thrombogenesis inhibitor on said adhered base coat layer, said thrombogenesis inhibitor being other than hirudin or an analog or fragment of hirudin.

17. The method of claim 16 wherein said immobilizing step further comprises immobilizing a thrombogenesis inhibitor selected from the group consisting of streptokinase, urokinase, tissue plasminogen activator, ATPase, ADPase, 5'-nucleotidase, and active fragments, and active analogs thereof, and mixtures thereof.

18. The method of claim 16 wherein said adhering step comprises:
   (a) activating said material so as to enhance the binding of said base coat layer thereto; and
   (b) contacting said activated material with said base coat layer for a time sufficient to allow said component of said base coat layer to bind to said activated material.

19. The method of claim 18 wherein said adhering step comprises adhering a base coat to at least one surface of a synthetic, polymeric, biocompatible material, said base coat layer containing a component selected from the group consisting of a protein, peptide, lipoprotein, glycoprotein, glycosaminoglycan, hydrogel, synthetic polymers, and mixtures thereof.

20. The method of claim 19 wherein said adhering step further comprises adhering a base coat layer containing a protein to at least one surface of said material.

21. The method of claim 20 wherein said adhering step further comprises adhering a base coat layer to at least one surface of said material, said base coat layer containing a protein selected from the group consisting of serum albumin, fibronectin, and mixtures thereof.

22. The method of claim 21 wherein said adhering step further comprises adhering a base coat layer containing human serum albumin to at least one surface of said material.

23. The method of claim 21 wherein said adhering step further comprises adhering a base coat layer containing bovine serum albumin to at least one surface of said material.

24. The method of claim 21 wherein said adhering step further comprises adhering a base coat layer containing human fibronectin to at least one surface of said material.

25. The method of claim 21 wherein said adhering step further comprises adhering a base coat layer containing bovine fibronectin to at least one surface of said material.

26. The method of claim 18 wherein said activating step comprises the steps of:
(a) treating said material with a solution that makes available for binding at least one chemically active group in said material; and
(b) contacting said treated material with a solution containing a bifunctional cross-linking reagent for a time sufficient to allow binding of said group to said reagent.

27. The method of claim 26 wherein said treating step further comprises treating said material with a solution that makes available for binding at least one carboxylic acid group in said material.

28. The method of claim 18 further comprising the preliminary step of contacting said material with a solution which removes impurities thereon, said preliminary step being performed prior to said adhering step.

29. The method of claim 18 wherein said immobilizing step further comprises the steps of:
(a) contacting said thrombogenesis inhibitor with a at least one molecule of a bifunctional cross-linking reagent for a time sufficient to allow linking of said reagent to said thrombogenesis inhibitor; and
(b) binding said thrombogenesis inhibitor-linked reagent to said base coat layer.

30. The method of claim 29 wherein said contacting step further comprises contacting said base coat with at least one molecule of said bifunctional cross-linking reagent for a time sufficient to allow linking of said agent to said base coat,
and said binding step further includes binding said thrombogenesis inhibitor-linked reagent to said base coat-linked reagent.

31. The method of claim 29 wherein said contacting step further includes contacting said thrombogenesis inhibitor with at least one molecule of said bifunctional cross-linking reagent selected from the group consisting of heterobifunctional cross-linking reagents, homobifunctional cross-linking reagents, and mixtures thereof.

32. The method of claim 30 wherein said contacting step includes contacting said base coat with at least one molecule of said bifunctional cross-linking reagent selected from the group consisting of heterobifunctional cross-linking reagents, homobifunctional cross-linking reagents, and mixtures thereof.

33. The method of claim 30 further comprising the steps of:
(a) reducing said base coat-linked reagent to expose a first sulfhydryl group thereon;
(b) adding said inhibitor-linked reagent to said exposed sulfhydryl group thereon; and
(c) inducing a substitution reaction involving said sulfhydryl group and said inhibitor-linked reagent, said reaction resulting in linkage of said base coat to said inhibitor.

34. The method of claim 31 wherein said contacting step includes contacting said thrombogenesis inhibitor with the heterobifunctional cross-linking reagent, N-succinimidyl 3-(2-pyridylaithio)propionate (SPDP).

35. The method of claim 32 wherein said contacting step includes contacting said thrombogenesis inhibitor with the heterobifunctional crosslinking reagent, SPDP.

36. The method of claim 29 further comprising the additional step of subjecting said throbogenesis-linked reagent to a chromatographic procedure to remove impurities therein, said additional step being performed after said contacting step and prior to said binding step.

37. A method of producing a biocompatible, thromboresistant substance, said method comprising the steps of:
(a) immobilizing a thrombogenesis inhibitor to a base coat layer,
said inhibitor being other than hirudin or an active analog or fragment of hirudin, and
said base coat layer containing a component capable of binding said thrombogenesis inhibitor; and
(b) adhering said base coat layer linked to said thrombogenesis inhibitor to at least one surface of a synthetic, polymeric, biocompatible material.

* * * * *